United States Patent [19]

Kano et al.

[11] Patent Number: 4,814,476
[45] Date of Patent: Mar. 21, 1989

[54] LIQUID CRYSTALLINE COMPOUND

[75] Inventors: Mitsuru Kano, Furukawa; Jun Nakanowatari, Kitaura, both of Japan

[73] Assignee: Alps Electric Co., Ltd., Japan

[21] Appl. No.: 101,773

[22] Filed: Sep. 28, 1987

Related U.S. Application Data

[62] Division of Ser. No. 914,284, Oct. 2, 1986, Pat. No. 4,697,015.

[30] Foreign Application Priority Data

Oct. 4, 1985 [JP] Japan .................................. 221552

[51] Int. Cl.$^4$ .................... C07D 239/32; C07C 63/06; C07C 69/017; C07C 69/78
[52] U.S. Cl. .................................. 558/416; 544/335; 560/59; 560/102
[58] Field of Search ................... 558/416; 560/59, 102

[56] References Cited

U.S. PATENT DOCUMENTS

Re. 31,715 10/1984 Coates et al. ................. 350/346
4,697,015 9/1987 Kano et al. ................. 544/335

Primary Examiner—Mary C. Lee
Assistant Examiner—J. Richter
Attorney, Agent, or Firm—Guy W. Shoup; Paul J. Winters; Stephen L. Malaska

[57] ABSTRACT

A liquid crystalline compound represented by the following general formula:

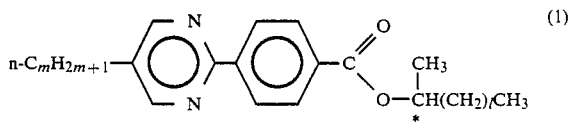

where m and l represent individually integers within a range: $6 \leq m \leq 14$ and $1 \leq l \leq 5$, the symbol * represents an asymmetric carbon atom and the compound is required to be optically active. The compound can induce the twisting arrangement when added to the TN system or phase transition type liquid crystal mixture, as well as can improve the spontaneous polarization as the index of the ferroelectric property when added to the SmC* liquid crystal mixture.

3 Claims, No Drawings

LIQUID CRYSTALLINE COMPOUND

This is a divisional application based on copending application serial No. 914,284 now U.S. Pat. No. 4,697,015 filed 10/2/86

BACKGROUND OF THE INVENTION

1. Field of the Invention

This invention concerns a liquid recrystalline compound for use in liquid crystal devices and, particularly, it relates to a novel optically rotating (chiral) substance inducing the twisting arrangement in liquid crystals.

2. Description of the Prior Art

As the operation principle for the liquid crystal display device, a twisting nematic (TN) system using a nematic liquid crystal phase, a phase transition system using a cholesteric liquid crystal phase, etc have been known. In any of these systems, a liquid crystal mixture incorporated with a chiral substance has been used with an aim of inducing the twisting arrangement in the liquid crystals. Further, an attention has been attracted to a high speed light switching device by using smectic liquid crystals, particularly, smectic C* (SmC*) liquid crystal phase characterized in the twisting arrangement and utilizing the ferroelectric property thereof in recent years. In this device, an SmC* liquid crystal compound which is the chiral substance or a SmC* liquid crystal mixture incorporated with a chiral substance is used.

In this way, a chiral substance inducing the twisting arrangement is extremely important for the liquid crystal display device or the like. However, the chiral substance for use in the liquid crystal display device or the like has been required not only to have a property of optical rotation but also it is important therefor that the substance itself has a liquid crystal property or that such property is not significantly reduced when it is added to a liquid crystal mixture. Further, it is desired that the compound has a great optical rotation attributable to the induction of the twisting arrangement. That is, the following requirements (1) and (2) are considered desirable as the properties of the chiral substance:

(1) The chiral substance has a liquid crystal property or does not significantly reduce the liquid crystal property of a liquid crystal mixture when the substance is added to the mixture.

(2) The substance has a high optical rotation.

However, there have been not so many kinds of chiral substance that can sufficiently satisfy the foregoing requirements.

SUMMARY OF THE INVENTION

Accordingly, it is an object of this invention to provide a novel liquid crystalline compound capable of satisfying the requirements (1) and (2) above simultaneously in view of the problems in the prior art as described above.

The present inventors have made an earnest study for attaining the foregoing object and found that the compound represented by the following general structural formula (1) has an excellent property as the chiral substance and have accomplished this invention. That is, this invention provides a liquid crystalline compound represented by the following general structure formula (1):

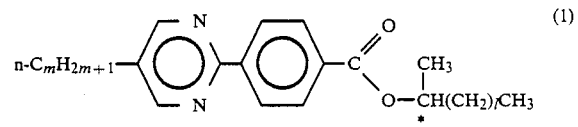

where m and l represent individually integers within a range: $6 \leq m \leq 14$ and $1 \leq l \leq 5$ and * represents an asymmetric carbon atom and the compound is required to be optically active.

Description will now be made as two whether the compound represented by the above general structural formula (1) can satisfy the requirements (1) and (2) above or not. Regarding the requirement (1), it can be seen that the requirement is satisfied since the main skelton has a pyrimidyl phenyl structure as the liquid crystal skelton, an asymmetric carbon atom represented by the symbol * developing the optical rotation is disposed near the middle of the skelton and an alkyl chain is disposed at the terminal end. Further, regarding the requirement (2) above, since the oxygen atom is directly bonded to the asymmetric carbon to improve the optical rotation, the requirement can also be satisfy.

The compound according to this invention represented by the foregoing general formula (1) can be synthesized, for example, by the following synthesis route.

(a) Synthesis Example of

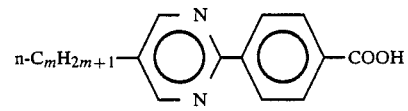

(4'-n-alkyl-4-alkylpyrimidyl phenyl carboxylic acid)

After refluxing commercially available

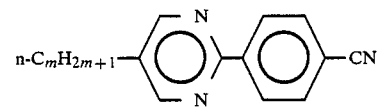

(4'-n-alkyl-4-cyanopyrimidyl phenyl) together with potassium hydroxide in diethylene glycol, the reaction solution is added to and stirred in a mixed solvent of methanol-concentrated hydrochloric acid at 2:1 ratio. The resultant crystals are filtered and then recrystallized from ethanol.

(b) Synthesis for

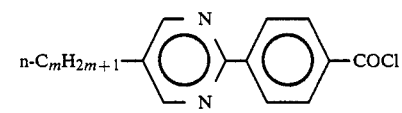

(acid chloride from (a) above)

After refluxing the compound in (a) together with thionyl chloride, excess thionyl chloride was removed by distillation.

(c) Synthesis of the compound represented by the general formula (1)

Commercially available optically active 2-alkyl alcohol:

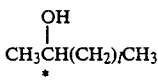

and 3 molar amount of a mixed solvent of pyridine and toluene is heated under stirring, to which an equimolar amount of the compound in (b) above is gradually added. Then, ordinary washing with acid, alkali and water is carried out, toluene is removed under distillation and then an aimed product is re-crystallized from ethanol.

The compound of the general formula (1) according to this invention having thus been synthesized can satisfy both of the requirements (1) and (2) above. Accordingly, the compound can be utilized for the liquid crystal mixture for constituting the liquid crystal display device or the like in the TN system or phase transition system. Further, it can also be utilized to a SmC* liquid crystal mixture improved with the spontaneous polarization as the index of the ferroelectric property (index for the increased speed)

DESCRIPTION OF THE PREFERRED EMBODIMENTS

EXAMPLE 1

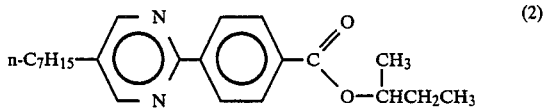

(Synthesis of (−)-4'-heptylpyrimidyl phenyl carboxylic acid 2-butanol ester)

(a) Commercially available 4'-n-heptyl-4-cyanopyrimidyl phenyl was refluxed by 20 g together with 10 g of potassium hydroxide in 100 ml of diethylene glycol for about three days. Then, the reaction solution was poured into a liquid mixture of 1000 ml of methanol and 500 ml of concentrated hydrochloric acid and stirred under heating for one-half day. The deposited crystals were collected by filtration, throughly washed with water and then recrystallized from ethanol for three times. The yield was about 20 g.

(b) 20 g of the compound obtained in the procedure (a) above was mixed with 30 ml of thionyl chloride and refluxed for about two hours. Then, excess thionyl chloride was removed by distillation under a reduced pressure.

(c) 19.5 g of the compound (b) above was gradually added under heating and stirring to a liquid mixture of 2.3 g of commercially available optically active (−)-2-butanol, 7.3 g of pyridine and 200 ml of toluene. Then, after continuing the reflux and stirring for one-half day, the reaction solution was washed with 8N-HCl, 2N-NaOH and water in this order, followed by removal of toluene under distillation. The crude products were crystallized from ethanol. The thus obtained compound was confirmed to be the compound represented by the formula (2) described above from the result of IR, $^{13}C$-NMR and liquid chromatography. The compound had a melting point of 0° C. and a specific rotation $[\alpha]_D^{26} = -20°$.

When the compound was added by 1% weight ratio to 100% of a commercially available biphenyl series liquid crystal mixture and then poured into a TN system liquid crystal display device cell, a liquid crystal display device showing a preferred operation could be obtained. Further, when the compound was added by from 2 to 3% by weight ratio to 100% of the similar liquid crystal mixture and poured into the cell of the liquid crystal display device, the liquid crystal display device of the white tailor type phase transition system could also be obtained.

EXAMPLE 2

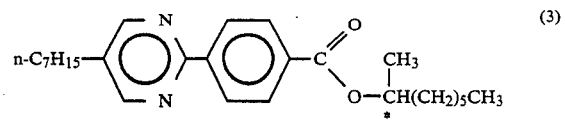

((−)-4'-heptylpyrimidyl phenyl carboxylic acid 2-octanol ester) was synthesized in the same procedures as in Example 1 except for using (−)-2-octanol instead of (−)-butanol in (c) of Example 1. The compound had a melting point at 2° C. and the specific rotation of $[\alpha]_D^{26} = -39.6°$.

EXAMPLES 3, 4

The following optical isomers (4) and (5) were synthesized in the same procedures as in Example 1 except for using (+)-2-butanol and (+)-2-octanol instead of (−)-2-butanol in (c) of Example 1 and (−)-2-octanol of Example 2:

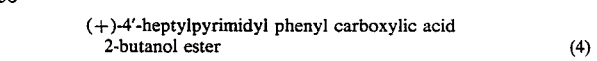

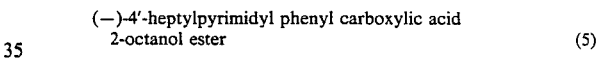

The melting points of the compounds (4) and (5) above were identical with those of the compounds of the corresponding optical isomers (2) and (3) respectively.

The specific rotation was as described below:
compound (4): $[\alpha] = +20.1°$
compound (5): $[\alpha] = +39.6°$ When these compounds were added each by 1% by weight ratio to 100% of the commercially available biphenyl series liquid crystal mixture and poured into the cell for use in TN system liquid crystal display device, a liquid crystal display device showing desirable operation could be obtained. Further, when these compounds were added each by 2–3% by weight ratio to 100% of the similar liquid crystal mixture and poured into the cell for use in a liquid crystal display device, a liquid crystal display device of white tailor type phase transition system could also be obtained.

EXAMPLE 5

The compounds C and D and the compound (2) obtained in Example 2 were selectively added respectively to the compounds A, B as the base mixture to prepare SmC* liquid crystal mixtures as shown in Table 1. Table 1 shows the SmC* temperature region and the spontaneous polarization Ps value of the liquid crystal mixing portion. As shown in Table 1, the effect of the compound (3) obtained in Example 2 for increasing the Ps value was extremely great. Further, similar effect of increasing the Ps value could also be confirmed with respect to the compounds (2), (4)–(5) obtained in Examples 3–9.

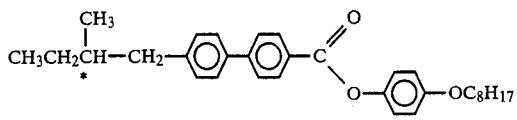

4'-(+)-amylbiphenyl carboxylic acid p-octyloxy phenol ester

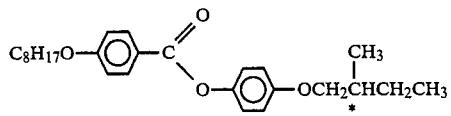

p-octyloxy phenyl carboxylic acid p'-amyloxy phenol ester

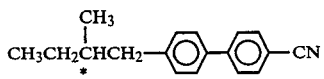

(+) 4'-amyl-4-cyanobiphenyl

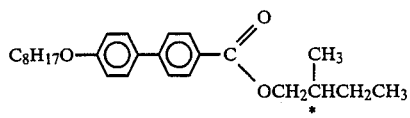

(+-(4'-octyloxy biphenyl carboxylic acid amyl alcohol ester

TABLE 1

| | Composition | SmC* temperature range | Ps(nC/cm²) |
|---|---|---|---|
| Comparative Example 1 | A:B = 40:60 | +10° C.~+60° C. | 1.5 |
| Comparative Example 2 | A:B = 40:60 + C 5% | +5° C.~+20° C. | 1.5 |
| Comparative Example 3 | A:B = 40:60 + D 5% | +3° C.~+50° C. | 4 |
| Example 1 | A:B = 40:60 + (3) 5% | +3° C.~+48° C. | 15 |

As has been described above, this invention can provide a chiral liquid crystalline compound having a liquid crystalline property per se or such a property as not significantly reducing the liquid crystal property of a liquid crystal mixture when added to such mixture, as well as having a high optical rotation. Accordingly, it can induce the twisting arrangement when added to the TN system liquid crystal mixture or phase transition system liquid crystal mixture. Further, the chiral substance can be added to the SmC* liquid crystal mixture to improve the spontaneous polarization which is the index for the ferro-electric property.

What is claimed is:

1. A liquid crystalline compound wherein the compound is 4'-(+)-amylbiphenyl carboxylic acid-p-octyloxy phenol ester.

2. A liquid crystalline compound, wherein the compound is (+)-4'-amyl 4-cyanobiphenyl.

3. A liquid crystalline compound, wherein the compound is (+)-4'-octyloxy biphenyl carboxylic acid amy-lalcohol ester.

* * * * *